(12) United States Patent
Fukumoto et al.

(10) Patent No.: US 9,028,669 B2
(45) Date of Patent: May 12, 2015

(54) PROCESS FOR PRODUCING REDUCED GLUTATHIONE

(71) Applicant: Kyowa Hakko Bio Co., Ltd., Tokyo (JP)

(72) Inventors: Kenta Fukumoto, Hofu (JP); Mitsutaka Kino, Hofu (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 0 days.

(21) Appl. No.: 14/046,864

(22) Filed: Oct. 4, 2013

(65) Prior Publication Data

US 2014/0027302 A1    Jan. 30, 2014

Related U.S. Application Data

(63) Continuation of application No. PCT/JP2012/059208, filed on Apr. 4, 2012.

(30) Foreign Application Priority Data

Apr. 6, 2011    (JP) .................. 2011-084358

(51) Int. Cl.
*C25B 3/00* (2006.01)
*C25B 3/04* (2006.01)
*C07K 5/02* (2006.01)

(52) U.S. Cl.
CPC ............. *C25B 3/04* (2013.01); *C07K 5/0215* (2013.01)

(58) Field of Classification Search
CPC ............... C25B 3/04; C07K 5/08; C07K 1/02
USPC ........................ 205/435, 443, 444
See application file for complete search history.

(56) References Cited

U.S. PATENT DOCUMENTS

2012/0118756 A1    5/2012    Fukumoto

FOREIGN PATENT DOCUMENTS

| CN | 101429229 A | * | 5/2009 | ............ C07K 5/037 |
|---|---|---|---|---|
| JP | 52-131527 A | | 11/1977 | |
| JP | 52-131528 A | | 11/1977 | |
| JP | 52131528 A | * | 11/1977 | ............ C07C 103/52 |
| JP | 59-009184 A | | 1/1984 | |
| JP | H08-041671 A1 | | 2/1996 | |
| JP | 2007-254324 A | | 10/2007 | |

(Continued)

OTHER PUBLICATIONS

Pereira-Rodrigues et al., "Electrocatalytic Activity of Cobalt Phthalocyanine CoPc Adsorbed on a Graphite Electrode for the Oxidation of Reduced L-Glutathione (GSH) and the Reduction of Its Disulfide (GSSG) at Physiological pH", Bioelectrochemistry (no month, 2007), vol. 70, pp. 147-154.*

(Continued)

*Primary Examiner* — Edna Wong
(74) *Attorney, Agent, or Firm* — Leydig, Voit & Mayer, Ltd.

(57) ABSTRACT

Reduced glutathione is produced by a process for producing reduced glutathione by electroreduction of oxidized glutathione using a cathode cell and an anode cell separated from each other by a separating membrane, comprising using, as a solution in the cathode cell, an aqueous oxidized glutathione solution having a pH adjusted to higher than 3.0 and not more than 7.0 by adding a base, in which oxidized glutathione itself also acts as a conducting agent.

14 Claims, 2 Drawing Sheets

(56) References Cited

FOREIGN PATENT DOCUMENTS

JP 2007-254325 A 10/2007
WO WO 2010/140625 A1 12/2010

OTHER PUBLICATIONS

Sakane et al., "Electrochemical Behavior of Glutathione (oxidized form) on a Mercury Electrode", Nippon Kagaku Kaishi (no month, 1982), vol. 1, pp. 81-86. Abstract Only.*

Sakane et al., "Electrochemical Behavior of Glutathione (oxidized form) on a Mercury Electrode", Nippon Kagaku Kaishi (no month, 1982), vol. 1, pp. 81-86.*
Japanese Patent Office, International Search Report in International Patent Application No. PCT/JP2012/059208 (Jun. 19, 2012).
Wan Fang, "Metal Ion Affinity Chromatography Separation and Purification of Glutathione," Academic Dissertation (Master Thesis) for Hubei University of Technology (May 1, 2006 with on-line publication date of Jun. 11, 2007).
European Patent Office, Supplementary European Search Report in European Patent Application No. 12 76 8186 (Dec. 2, 2014).

* cited by examiner

PROCESS FOR PRODUCING REDUCED GLUTATHIONE

CROSS-REFERENCE TO RELATED APPLICATIONS

This application is a continuation of International Patent Application No. PCT/JP2012/059208, filed on Apr. 4, 2012, which claims priority to Japanese Patent Application No. 2011-084358, filed on Apr. 6, 2011, both of which are incorporated by reference in their entireties herein.

TECHNICAL FIELD

The present invention relates to a process for producing reduced glutathione by electroreduction of oxidized glutathione.

BACKGROUND ART

As a method of electroreduction of a disulfide compound, a method using an alloy consisting of two or more kinds of particular metals as a cathode is known (patent document 1). In addition, as a process for producing L-cysteine by electroreduction of L-cystine, which is one kind of disulfide compound, a method using a cation exchange membrane as a separating membrane, and an L-cystine solution acidified by adding a mineral acid such as hydrochloric acid and the like to a cathode side electrolytic cell is known (patent document 2). As a process for producing reduced glutathione by electroreduction of oxidized glutathione, a method using an aqueous oxidized glutathione solution acidified by adding a mineral acid such as concentrated hydrochloric acid and the like to a cathode side electrolytic cell is also known (patent document 3).

However, the above-mentioned electroreduction methods of a disulfide compound require use of an expensive electrode. When oxidized glutathione is electroreduced under L-cystine electroreduction conditions described in patent document 2, reduced glutathione cannot be produced in a sufficient yield, since it is unstable under strong acidity and high temperature, as compared to L-cysteine. The process described in patent document 3 also uses, similar to the process described in patent document 2, aqueous oxidized glutathione solution strongly acidified to pH 0.6-1.0 by adding a mineral acid, and therefore, it is associated with the problems of corrosion of cathode and decomposition of reduced glutathione. To minimize the decomposition of reduced glutathione under strong acidity, it is necessary to lower the electric current density. In this case, however, reduction efficiency per electrode area decreases, and therefore, efficient production of reduced glutathione cannot be achieved unless the electrode area is increased instead. That is, production of reduced glutathione in an industrial scale by electroreduction of aqueous oxidized glutathione solution strongly acidified with a mineral acid requires huge electroreduction facility corresponding to the sizes of ion exchange membrane and electrode, as well as a special electrode capable of resisting corrosion. Therefore, a process for producing reduced glutathione by conventional electroreduction is not entirely a realistic method in terms of production efficiency and facility.

To perform electrolysis with good reduction efficiency, which can be practiced on an industrial scale, use of an oxidized glutathione solution with a high concentration is desirable. Patent document 4 describes an electroreduction method utilizing supersaturation of oxidized glutathione, wherein the efficiency of electroreduction is enhanced by this method by using oxidized glutathione at a high concentration, whereby realistic electroreduction in terms of production efficiency and facility can be performed. However, when oxidized glutathione is electroreduced in a supersaturation region, glutathione is rapidly crystallized and precipitated due to the applied voltage, agitation, shock by spray drying, and the like, and the precipitated glutathione crystal may obstruct the electrolytic cell. In addition, since it is an electroreduction in an acidic region, corrosion of cathode is inevitable.

For industrial electroreduction of oxidized glutathione, it is important to continue electroreduction using high concentration oxidized glutathione solution while avoiding corrosion of cathode and without permitting crystallization of oxidized glutathione and reduced glutathione.

DOCUMENT LIST

Patent Documents patent document 1: JP-A-H8-41671
patent document 2: JP-A-S59-9184
patent document 3: JP-A-S52-131528
patent document 4: WO2010/140625

SUMMARY OF THE INVENTION

Problems to be Solved by the Invention

In a process for producing reduced glutathione by electroreduction of oxidized glutathione, improvement of reduction efficiency is demanded to reduce the necessary areas of electrode and ion exchange membrane to realistic sizes, while suppressing the corrosion of cathode, decomposition of reduced glutathione and crystallization of glutathione.

Means of Solving the Problems

The present invention relates to the process described in the following (1)-(6).

(1) A process for producing reduced glutathione by electroreduction of oxidized glutathione using a cathode cell and an anode cell separated from each other by a separating membrane, comprising using, as a solution in the cathode cell, an aqueous oxidized glutathione solution having a pH adjusted to higher than 3.0 and not more than 7.0 by adding a base.
(2) The process according to the above-mentioned (1), wherein the base is sodium or potassium salt of hydroxide, carbonate or hydrogencarbonate.
(3) The process according to the above-mentioned (1) or (2), wherein the aqueous oxidized glutathione solution does not contain a neutral salt as a conducting agent.
(4) The process according to any one of the above-mentioned (1) to (3), wherein the aqueous oxidized glutathione solution has a concentration of not less than 20 g/L.
(5) The process according to any one of the above-mentioned (1) to (4), wherein the electroreduction is carried out at an electric current density of 0.1-30 A/dm$^2$.
(6) A process for producing a reduced glutathione crystal, comprising subjecting a reduced glutathione solution produced by the process according to any one of the above-mentioned (1) to (5) to 1) adjustment of pH, or 2) removal of cation by passing the solution through an ion exchange column, followed by crystallization.

Effect of the Invention

The present invention can produce reduced glutathione efficiently in an industrial scale.

DESCRIPTION OF EMBODIMENTS

The process of the present invention is, in a method of producing reduced glutathione by electroreduction of oxidized glutathione using a cathode cell and an anode cell separated from each other by a separating membrane, a method comprising using, as a solution in the cathode cell, an aqueous oxidized glutathione solution having a pH adjusted to higher than 3.0 and not more than 7.0 by adding a base.

Examples of the base include bases capable of neutralizing an aqueous oxidized glutathione solution, preferably bases containing alkali metal ions such as sodium, potassium and the like, alkaline earth metal ions such as calcium and the like, ammonium ion, imidazolium ion, and phosphonium ion, more preferably bases containing alkali metal ion, particularly preferably bases containing a cation of sodium and potassium. The aforementioned base containing cation may have any form such as forms of hydroxide, carbonate, hydrogencarbonate and the like, and the method of adjusting pH is not limited and pH can be adjusted by a known method.

The pH of the aqueous oxidized glutathione solution is preferably higher than 3.0 and not more than 7.0, more preferably pH 4.0-7.0, particularly preferably pH 5.0-7.0, since reduced glutathione produced by electroreduction is decomposed under strong acidity and basicity.

Figure 1:
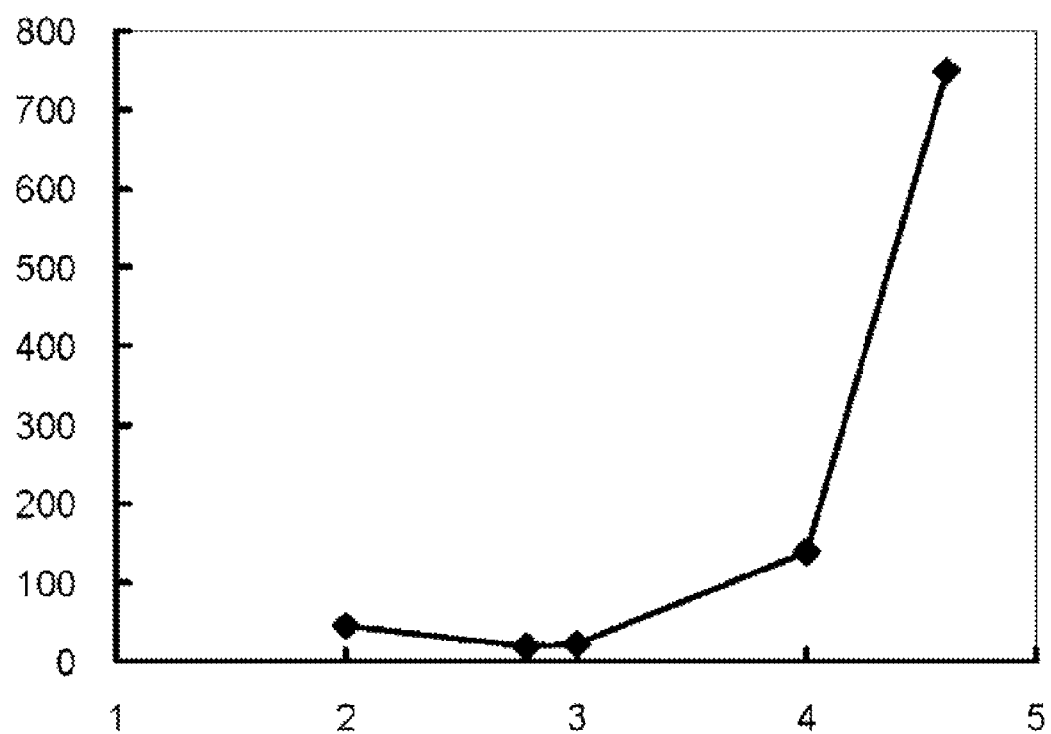
FIG. 1 shows solubility of oxidized glutathione at each pH, wherein the vertical axis shows solubility of oxidized glutathione in water at 25° C. (g/L), and the horizontal axis shows pH.

While the saturated solubility of oxidized glutathione at the isoelectric point in water at ambient temperature (25° C.) is not more than 20 g/L, the solubility becomes high by increasing pH (FIG. 1). When the concentration of oxidized glutathione in the cathode cell is higher, the conductivity is improved more, and oxidized glutathione is supplied to the surface of an electrode more smoothly, and thus the efficiency of electroreduction becomes higher. The process of the present invention, electroreduction can be performed efficiently without crystallization due to shock by energization during electroreduction and the like, by adjusting pH of the aqueous oxidized glutathione solution to a pH higher than that at the isoelectric point of the oxidized glutathione to prepare an aqueous oxidized glutathione solution with a high concentration. Furthermore, elution of the electrode by an acid can be suppressed since electroreduction can be performed under weak acidity to neutrality.

Since use of an oxidized glutathione salt itself, which is produced by adding a base to an aqueous oxidized glutathione solution, as a conducting agent can improve the electrical conductivity of the solution, the impedance of the solution is low, and therefore, the temperature of the aqueous solution does not become high. That is, the decomposition of reduced glutathione in a cathode cell can be suppressed. Since the oxidized glutathione salt itself becomes a conducting agent, addition of inorganic salts such as neutral salt (e.g., sodium sulfate and the like) as the conducting agent is not necessary, therefore after completion of the electroreduction reaction, it is only necessary to remove the base used for adjusting pH, and the removal itself is easy.

As mentioned above, since the production efficiency of reduced glutathione can be improved while suppressing the decomposition thereof by electroreduction of an aqueous oxidized glutathione solution, which is adjusted to a pH higher than 3.0 and not more than 7.0 by adding a base, in a cathode cell, therefore, the separating membrane and electrode can be downsized, and thus reduced glutathione can be produced economically.

In the process of the present invention, since an aqueous oxidized glutathione solution, which is adjusted to a pH higher than 3.0 and not more than 7.0 by adding a base, is used as an aqueous solution for a cathode cell, it is also a method using an aqueous oxidized glutathione solution with a high concentration but in an unsaturated state as a cathode cell solution. While the concentration of the aqueous oxidized glutathione solution is not limited, it is 20 g/L or more, preferably 100 g/L or more, more preferably 200 g/L or more, further preferably 300 g/L or more, most preferably 400 g/L or more.

The solution for an anode cell in the present invention is not particularly limited as long as it is a conductive aqueous solution, and inorganic acid solutions such as hydrochloric acid and sulfuric acid, organic acid solutions such as acetic acid and propionic acid, a solution dissolving a conducting agent other than acid and the like can be mentioned. As for the concentration of inorganic acid and organic acid, conductivity is low at low concentrations, and ion exchange membrane is easily deteriorated at high concentrations. Therefore, the concentration thereof to be used is 0.5-3 mol/L, preferably 1-2 mol/L.

As the cathode used in the process of the present invention, a metal or alloy having a high hydrogen overvoltage is preferably used. Examples of such metal include zinc and lead, more preferably zinc. Examples of the cathode material other than metal include carbon electrode such as carbon (graphite, glassy carbon, conductive diamond), porous carbon, and fibrous carbon (carbon felt, carbon cloth, carbon paper). Examples of the shape of the electrode, but are not limited to, plate-shaped, net-like, fibrous and the like.

As the anode to be used in the process of the present invention, any metal can be used as long as it is an insoluble metal. A metal superior in the corrosion resistance is preferable and, for example, titanium plated with platinum, platinum-iridium, lead, lead alloy, lead dioxide, gold and titanium oxide can be mentioned. Preferred is titanium plated with platinum.

As the separating membrane to be used in the process of the present invention, any membrane can be used as long as it can reduce leakage of reduced glutathione produced in the cathode cell into the anode cell. Preferred is an ion exchange membrane, more preferred is a cation exchange membrane, specifically SELEMION CMT (manufactured by Asahi Glass Company) or Nafion (manufactured by DuPont)

In the process of the present invention, electric current density, voltage, temperature and the like are not particularly limited. As conditions for improving reduction efficiency while suppressing decomposition of the produced reduced glutathione, the electric current density is preferably 0.1-30 A/dm$^2$, more preferably 0.5-20 A/dm$^2$, further preferably 1-10 A/dm$^2$, the voltage is preferably 1-20 V, more preferably 2-15 V, further preferably 3-10 V, and the temperature is preferably 4-50° C., more preferably 10-30° C., further preferably 10-25° C.

After completion of electroreduction, a solution in the cathode cell which contains the produced reduced glutathione can be directly used for crystallization by adjusting pH to near the isoelectric point of reduced glutathione (pH 3.0) with various mineral acids such as sulfuric acid and hydrochloric acid. In addition, the solution in the cathode cell containing reduced glutathione is desalted by passing through an ion exchange column, and the aqueous desalted reduced glutathione solution may be directly used for crystallization. Examples of the ion exchange resin include strongly acidic cation exchange resins represented by SK-116 and SK-104 (both DIAIONs, manufactured by Mitsubishi Chemical Corporation), and weakly basic ion exchange resins represented by WA-30 and WA-21 (both DIAIONs, manufactured by Mitsubishi Chemical Corporation). The pH-adjusted or desalted reduced glutathione can be crystallized by concentration, appropriate addition of a solvent or seed crystal, and cooling.

Reference Example Solubility of Oxidized Glutathione

A crystal of oxidized glutathione (monohydrate) was added to 100 ml of water and the mixture was stirred at 25° C. for 4 hr. After measurement of pH, the solution was separated and filtered, and the dissolved oxidized glutathione was quantified by high performance liquid chromatography (HPLC) under the following conditions. Then, the crystal of oxidized glutathione was added to 1 mol/L of aqueous sodium hydroxide solution, and the mixture was stirred for 4 hr or longer while glutathione crystal slightly remained undissolved. After measurement of pH, the solution was separated and filtered, and the concentration was measured in the same manner.

As shown in FIG. 1, the solubility was the lowest in a solution at pH 2.0-3.0 near the isoelectric point of glutathione, and remarkably increased at not less than pH 4.0.

As the content, the concentration (g/L) of oxidized glutathione was quantified under the following HPLC conditions.

HPLC Conditions
column: Inertsil ODS-3 φ3×100 mm
column temperature: 35° C.
buffer: 3% methanol solution containing 0.2% sodium 1-heptanesulfonate, 6.8% potassium dihydrogen phosphate (adjusted to pH 3.0 with phosphoric acid)
flow rate: 0.5 mL/min
detector: UV detector (wavelength 210 nm)

EXAMPLE 1

Electroreduction of Oxidized Glutathione (1)

Sodium hydroxide was added to an aqueous oxidized glutathione solution to allow pH to be adjusted to 6.5, whereby 400 g/L aqueous oxidized glutathione solution was prepared. As the electrolytic cell, anode cell (15 L) and cathode cell (15 L) were used, and the both were separated by a cation exchange membrane SELEMION CMT (manufactured by Asahi Glass Company) with an effective membrane area of 1.8 dm². As the anode, a platinum-plated titanium plate was used, and as the cathode, a zinc plate was used. The distance between the electrode and the cation exchange membrane was set to 1.9 mm, and the circulation flow was set to 240 L/h. The anode cell contained 0.50 mol/L sulfuric acid solution (5 L), and the cathode cell contained the aqueous oxidized glutathione solution (400 g/L, 5 L) prepared above.

Electroreduction reaction was performed at electrolytic voltage 6V, electrolytic electric current 6.6-8.3 A/dm², and room temperature. The resultant product in the cathode cell was quantified by HPLC under the same conditions as in Reference Example, and production of 1.85 kg of reduced glutathione in 51 hr was confirmed (conversion ratio 92.6%).

The amount of zinc ion in the cathode cell solution after the completion of electrolysis was confirmed by Zeeman atomic absorption spectrophotometer (Z-2310 manufactured by Hitachi High-Technologies Corporation), whereby elution of 295 mg of zinc was confirmed.

EXAMPLE 2

Electroreduction of Oxidized Glutathione (2)

Sodium hydroxide was added to adjust pH of the solution to 4.5, whereby 400 g/L aqueous oxidized glutathione solution was prepared. Electroreduction was performed under the same conditions as in Example 1, whereby production of 1.73 kg of reduced glutathione in 52 hr was confirmed (conversion ratio 86.7%).

The amount of zinc ion in the cathode cell solution after the completion of electrolysis was confirmed in the same manner, whereby elution of 430 mg of zinc was confirmed.

EXAMPLE 3

Electroreduction of Oxidized Glutathione (3)

Using graphite electrode as cathode and an oxidized glutathione solution under the same conditions as in Example 1, an electroreduction reaction was performed at electrolytic voltage 6V, electrolytic electric current 6.6-8.3 A/dm², and room temperature. The resultant product in the cathode cell was quantified by HPLC under the same conditions as in Example 1 and 1.82 kg of reduced glutathione was confirmed to have been produced over 70 hr (conversion ratio 90.7%).

EXAMPLE 4

Production of Reduced Glutathione Crystals

The aqueous reduced glutathione solution obtained in Example 1 was passed through a strongly acidic cation exchange resin SK-116 (H+) (manufactured by Mitsubishi Chemical Corporation) to remove cation component (sodium). The obtained reduced glutathione solution was concentrated under reduced pressure, and a solvent and a seed crystal were added to give a crystal of reduced glutathione (yield 83%).

Comparative Example 1

Electroreduction Using Supersaturated Aqueous Oxidized Glutathione Solution

Sodium hydroxide was added to adjust pH to 7.0, whereby 300 g/L aqueous oxidized glutathione solution was prepared. Sulfuric acid was added to the solution to adjust pH to 2.91, and the mixture was diluted, sodium sulfate was added, whereby 150 g/L aqueous oxidized glutathione solution containing 100 g/L sodium sulfate was prepared. Using the solution as a cathode cell solution, electroreduction was performed under the same conditions as in Example 1. A crystal of oxidized glutathione was precipitated from the cathode cell solution in 1 hr from the start of the energization, and the precipitated crystal obstructed the pump for feeding into the electrolytic cell.

INDUSTRIAL APPLICABILITY

The process of the present invention has enabled an industrial scale production of reduced glutathione by electroreduction of oxidized glutathione.

[Explanation of Symbols]

Figure 2:
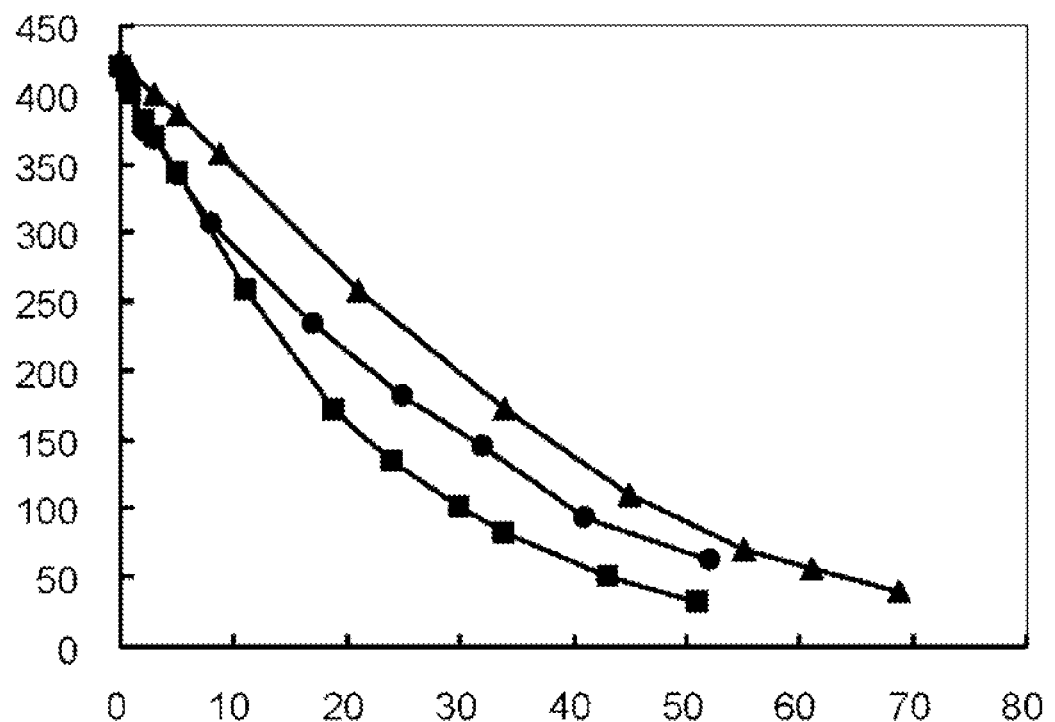
FIG. 2 shows the relationship between the concentration of oxidized glutathione in a cathode cell solution and the electroreduction rate, wherein the vertical axis shows the concentration of oxidized glutathione in a cathode cell solution (g/L) and the horizontal axis shows an electroreduction time (h).

On FIG. 2, ■ shows changes of concentration of oxidized glutathione by electroreduction at pH 6.5 using zinc electrode (Example 1), ● by electroreduction at pH 4.5 using zinc electrode (Example 2), and ▲ by electroreduction of aqueous oxidized glutathione solution at pH 6.5 using graphite electrode (Example 3).

The invention claimed is:

1. A process for producing reduced glutathione by electroreduction of oxidized glutathione using a cathode cell and an anode cell separated from each other by a separating membrane, comprising
   providing an aqueous oxidized glutathione solution in the cathode cell, wherein the aqueous oxidized glutathione solution in the cathode cell has a concentration of oxidized glutathione of not less than 200 g/L, and the aqueous oxidized glutathione solution does not contain a neutral salt as a conducting agent,
   adding a base to the aqueous oxidized glutathione solution to provide a pH of 4.0-7.0, and
   electroreducing the aqueous oxidized glutathione solution to provide reduced glutathione.

2. The process according to claim 1, wherein the base is sodium or potassium salt of hydroxide, carbonate or hydrogencarbonate.

3. The process according to claim 2, wherein the step of adding a base to the aqueous oxidized glutathione solution provides a pH of 4.5-7.0.

4. The process according to claim 2, wherein the step of adding a base to the aqueous oxidized glutathione solution provides a pH of 5.0-7.0.

5. The process according to claim 1, wherein the electroreduction is carried out at an electric current density of 0.1-30 A/dm$^2$.

6. The process according to claim 1, wherein the step of adding a base to the aqueous oxidized glutathione solution provides a pH of 4.5-7.0.

7. The process according to claim 1, wherein the step of adding a base to the aqueous oxidized glutathione solution provides a pH of 5.0-7.0.

8. A process for producing a reduced glutathione crystal, comprising
   (a) providing an aqueous oxidized glutathione solution, wherein the aqueous oxidized glutathione solution does not contain a neutral salt as a conducting agent,
   (b) adding a base to the aqueous oxidized glutathione solution to provide a pH of 4.0-7.0,
   (c) providing a cathode cell and an anode cell separated from each other by a separating membrane with the aqueous oxidized glutathione solution in the cathode cell, wherein the aqueous oxidized glutathione solution in the cathode cell has a concentration of oxidized glutathione of not less than 200 g/L,
   (d) electroreducing the aqueous oxidized glutathione solution to form a reduced glutathione solution, and
   (e) subjecting the reduced glutathione solution to (1) adjustment of pH, or (2) removal of cation by passing the solution through an ion exchange column, followed by crystallization.

9. The process according to claim 8, wherein the base is sodium or potassium salt of hydroxide, carbonate or hydrogencarbonate.

10. The process according to claim 9, wherein step (b) provides a pH of 4.5-7.0.

11. The process according to claim 9, wherein step (b) provides a pH of 5.0-7.0.

12. The process according to claim 8, wherein the electroreduction is carried out at an electric current density of 0.1-30 A/dm$^2$.

13. The process according to claim 8, wherein step (b) provides a pH of 4.5-7.0.

14. The process according to claim 8, wherein step (b) provides a pH of 5.0-7.0.

* * * * *